US011026851B2

(12) United States Patent
Saito et al.

(10) Patent No.: US 11,026,851 B2
(45) Date of Patent: Jun. 8, 2021

(54) ABSORBENT ARTICLE

(71) Applicant: UNICHARM CORPORATION, Shikokuchuo (JP)

(72) Inventors: Kyota Saito, Kanonji (JP); Jirapa Changcharoen, Chachoengsao (TH); Sarinee Pichadkitjawat, Chachoengsao (TH)

(73) Assignee: UNICHARM CORPORATION, Ehime (JP)

( * ) Notice: Subject to any disclaimer, the term of this patent is extended or adjusted under 35 U.S.C. 154(b) by 263 days.

(21) Appl. No.: 16/063,730

(22) PCT Filed: Sep. 27, 2016

(86) PCT No.: PCT/JP2016/078375
§ 371 (c)(1),
(2) Date: Jun. 19, 2018

(87) PCT Pub. No.: WO2017/115508
PCT Pub. Date: Jul. 6, 2017

(65) Prior Publication Data
US 2019/0231616 A1 Aug. 1, 2019

(30) Foreign Application Priority Data
Dec. 28, 2015 (JP) .............................. JP2015-256832

(51) Int. Cl.
*A61F 13/49* (2006.01)
*A61F 13/56* (2006.01)
*A61F 13/496* (2006.01)

(52) U.S. Cl.
CPC ...... *A61F 13/5655* (2013.01); *A61F 13/4963* (2013.01); *A61F 13/5638* (2013.01); *A61F 2013/49074* (2013.01)

(58) Field of Classification Search
CPC .. A61F 13/4963; A61F 13/56; A61F 13/5622; A61F 13/5638; A61F 13/5655;
(Continued)

(56) References Cited

U.S. PATENT DOCUMENTS 2,290,110 A 7/1942 McGraw
5,368,585 A * 11/1994 Dokken ............ A61F 13/15268
604/358
(Continued)

FOREIGN PATENT DOCUMENTS

CN 1308515 A 8/2001
CN 101657173 2/2010
(Continued)

OTHER PUBLICATIONS

International Search Report in PCT Application No. PCT/JP2016/078375, dated Dec. 13, 2016, 4pp.
(Continued)

*Primary Examiner* — Catharine L Anderson
(74) *Attorney, Agent, or Firm* — Hauptman Ham, LLP

(57) ABSTRACT

An absorbent article includes: a front waist portion extending along the lateral direction; a back waist portion extending along the lateral direction; and a crotch portion provided between the front waist portion and the back waist portion. A lateral end portion of the back waist portion on a one side and a lateral end portion of the front waist portion on the one side are joined by a first joining portion. The back waist portion has a fastening portion provided on another side in the lateral direction, and the fastening portion is capable of being fastened to the front waist portion when putting on the absorbent article. The front waist portion has a target region to which the fastening portion is to be fastened, and a lateral end of the target region on the one side is located on the one side relative to a lateral central position of the crotch portion.

10 Claims, 11 Drawing Sheets

(58) Field of Classification Search
CPC .. A61F 2013/49074; A61F 2013/49076; A61F 2013/49077; A61F 2013/5683; A61F 2013/5688
See application file for complete search history.

(56) References Cited

U.S. PATENT DOCUMENTS

| | | | | |
|---|---|---|---|---|
| 5,370,634 | A * | 12/1994 | Ando | A61F 13/49009 604/358 |
| 5,695,488 | A * | 12/1997 | Sosalla | A61F 13/49011 604/385.24 |
| 7,473,818 | B2 * | 1/2009 | Datta | A61F 13/49009 604/366 |
| 2004/0116888 | A1 * | 6/2004 | Dorschner | A61F 13/5655 604/385.22 |
| 2017/0303512 | A1 * | 10/2017 | Komatsubara | A01K 23/00 |
| 2018/0116178 | A1 * | 5/2018 | Komatsubara | A01K 23/00 |

FOREIGN PATENT DOCUMENTS

| | | |
|---|---|---|
| EP | 1600132 A1 | 11/2005 |
| JP | H4-5826 U | 1/1992 |
| JP | H8-308876 A | 11/1996 |
| JP | 2008-104874 A | 5/2008 |
| JP | 2014-506511 A | 3/2014 |
| WO | 2008/056278 A1 | 5/2008 |

OTHER PUBLICATIONS

Office Action in BR Application No. BR112018010777-8, dated May 14, 2020, 4pp.
Office Action in EP Application No. 16881488.7, dated Apr. 23, 2020, 8pp.
International Preliminary Report on Patentability in PCT Application No. PCT/JP2016/078375, dated Dec. 13, 2016, 16pp.
Office Action in JP Application No. 2015-256832, dated Aug. 7, 2018, 7pp.
Extended European Search Report in EP Application No. 16881488.7 dated Dec. 17, 2018, 6pp.
Office Action in CN Application No. 201680077455.0, dated Jul. 27, 2020, 17 pp.
Office Action in EP Application No. 16881488.7, dated Sep. 23, 2020, 4pp.
Office Action in AU Application No. 2016381778, dated Oct. 23, 2020, 4pp.
Office Action in CN Application No. 201680077455.0, dated Jan. 22, 2021, 11 pp.

* cited by examiner

ABSORBENT ARTICLE

RELATED APPLICATIONS

The present application is a national phase of International Application Number PCT/JP2016/078375, filed Sep. 27, 2016, which claims priority to Japanese Application Number 2015-256832, filed Dec. 28, 2015.

TECHNICAL FIELD

The present invention relates to an absorbent article.

BACKGROUND ART

A disposable diaper such as a so-called tape-type diaper or a pull-on disposable diaper is conventionally known as an absorbent article for absorbing excrement. These tape-type diapers and pull-on disposable diapers have a problem of difficulty in being put on a wriggling infant and a problem that the diapers force a wearer to take an unnatural posture when being put on. In order to solve these problems, PTL 1 discloses a half-open, underpants-shaped diaper in which portions on either one side of the left or right sides of the waist part are joined together, and portions on the other side are not joined together.

CITATION LIST

Patent Literature

[PTL 1] Japanese Unexamined Utility Model Application Publication No. H 4-5826

SUMMARY OF INVENTION

Technical Problem

When the half-open, underpants-shaped diaper disclosed in PTL 1 is to be put on, one leg of the wearer is first inserted into the leg hole of either one side of the left or right sides of the waist part. Thereafter, the front and back waist parts on the other side are pulled together so as to overlap, and a fastening portion (tape fastener; provided on the back waist part side) is joined to a target region (adhesion region; provided on the front waist part side). The front and back waist parts are thus fixed around the wearer's waist, and the diaper can be put on without forcing the wearer to take an unnatural posture.

However, in the half-open, underpants-shaped diaper disclosed in PTL 1, the target region to be fastened with the fastening portion is provided in only a partial region that is on the other side of the lateral center of the front waist portion. This does not make it possible to ensure a sufficiently large region that can be fastened with the fastening portion. This reduces adjustable range for the waist size of the diaper, and causes such problems that the fit around the waist is insufficient, and that the position of the diaper shifts after being put on.

The present invention was achieved in light of the problems described above, and an aspect of the present invention is to provide a half-open diaper that can provide a favorable fit around the waist of the wearer.

Solution to Problem

A main aspect of the invention for achieving the aforementioned object is an absorbent article having a longitudinal direction, a lateral direction intersecting the longitudinal direction, and a front-back direction intersecting the longitudinal direction and the lateral direction, the absorbent article including: a front waist portion extending along the lateral direction; a back waist portion extending along the lateral direction; and a crotch portion provided between the front waist portion and the back waist portion, a lateral end portion of the back waist portion on a one side and a lateral end portion of the front waist portion on the one side being joined by a first joining portion, the back waist portion having a fastening portion provided on another side in the lateral direction, the fastening portion being capable of being fastened to the front waist portion when putting on the absorbent article, the front waist portion having a target region, the target region being a region to which the fastening portion is to be fastened, and a lateral end of the target region on the one side being located on the one side relative to a lateral central position of the crotch portion.

Other features of the present invention will become apparent from the description of the present specification and the accompanying drawings.

Advantageous Effects of Invention

According to the present invention, it is possible to provide a half-open diaper that can provide a favorable fit around the waist of the wearer.

DESCRIPTION OF EMBODIMENTS

Figure 1:
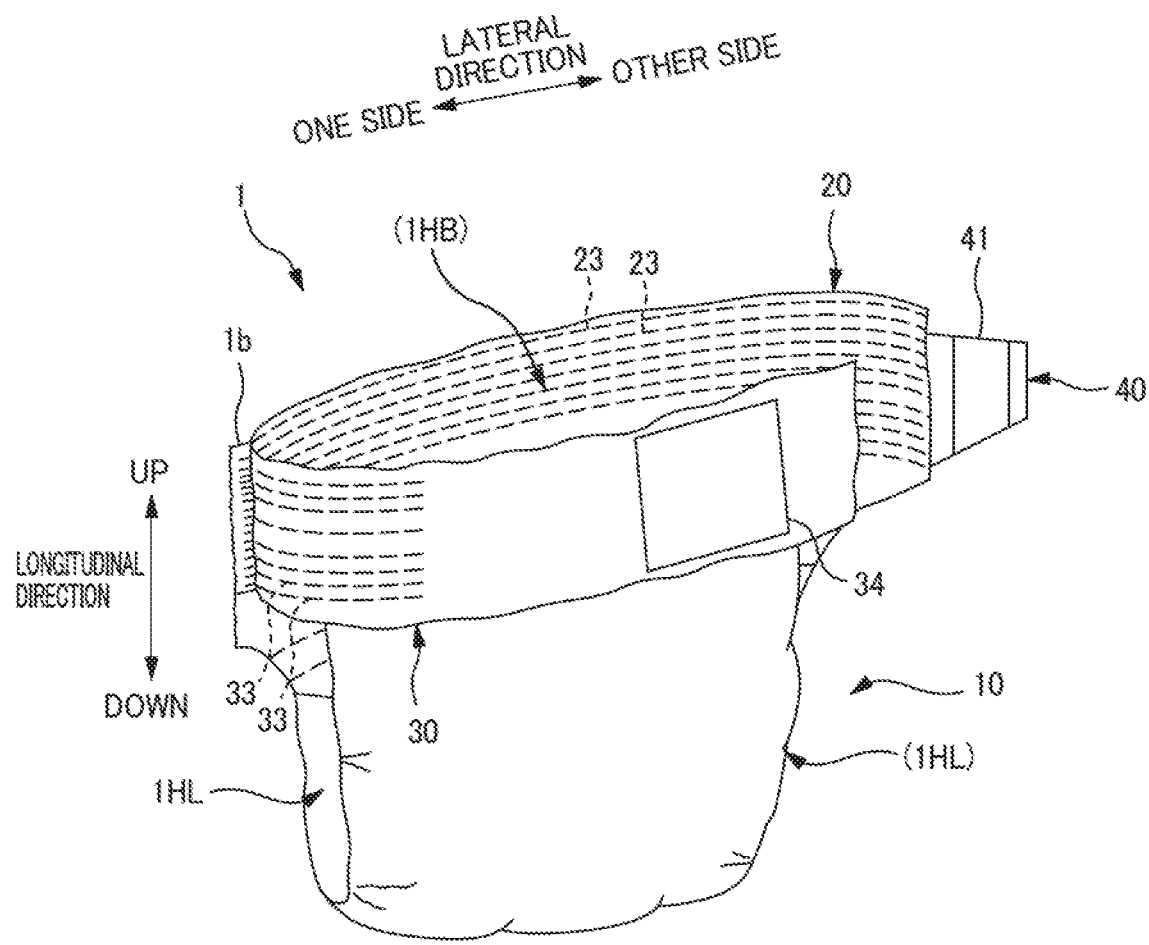
FIG. 1 is a schematic perspective view of a diaper 1 according to an embodiment.

At least the following matters will become apparent from the description of the present specification and the accompanying drawings.

An absorbent article having a longitudinal direction, a lateral direction intersecting the longitudinal direction, and a front-back direction intersecting the longitudinal direction and the lateral direction, the absorbent article including: a front waist portion extending along the lateral direction; a back waist portion extending along the lateral direction; and a crotch portion provided between the front waist portion and the back waist portion, a lateral end portion of the back waist portion on a one side and a lateral end portion of the front waist portion on the one side being joined by a first joining portion, the back waist portion having a fastening portion provided on another side in the lateral direction, the fastening portion being capable of being fastened to the front waist portion when putting on the absorbent article, the front waist portion having a target region, the target region being a region to which the fastening portion is to be fastened, and a lateral end of the target region on the one side being located on the one side relative to a lateral central position of the crotch portion.

According to this absorbent article, the fastening portion can be fastened up to a position located on the one side relative to the central position of the crotch portion. This makes it possible to adjust the size of the waist opening in a wide range, and makes it easier to give the wearer a favorable fit when putting on the absorbent article.

In the above absorbent article, it is desirable that the lateral end of the target region on the one side is between the lateral central position of the crotch portion and a position located on the one side away from the lateral central position a distance corresponding to a lateral length of the fastening portion.

According to this absorbent article, the region which the fastening portion can be fastened to is restricted from being excessively expanded to the one side in the lateral direction. This suppresses excessive increase of the area of the overlapping portions of the back waist portion and the front waist portion, making it is possible to prevent these overlapping portions from displacing to each other. This makes it possible to improve the fit and make positional shift difficult to occur when putting on the absorbent article.

In the above absorbent article, it is desirable that a lateral end of the target region on the other side is between the lateral central position of the crotch portion and a position located on the one side away from a lateral end of the front waist portion on the other side a distance corresponding to a lateral length of the fastening portion.

According to this absorbent article, it is possible to fasten the fastening portion in a wide range on the other side in the lateral direction. This makes it possible to adjust the size of the waist opening in a wide range, and makes it easier to give the wearer a favorable fit when putting on the absorbent article. In this case, limiting the fastenable range on the other side makes it possible to suppress the case where the fastening portion protrudes from the front waist portion to the other side and comes into contact with the wearer's skin. This makes it difficult to cause discomfort to the wearer when putting on the absorbent article.

In the above absorbent article, it is desirable that the lateral end of the target region on the other side is between the lateral central position of the crotch portion and a position of a lateral end of the crotch portion on the other side.

According to this absorbent article, the target region does not overlap with the lateral end portion of the crotch portion. Accordingly, a step generated on the lateral end portion due to the thickness of the crotch portion is less likely to have an influence on the target region, making the target region easier to keep flat. The fastening portion is therefore more easily fastened. Also, this reduces a possibility of the fastening portion protruding from the front waist portion to the other side, making it difficult to cause discomfort to the wearer.

In the above absorbent article, it is desirable
that the front waist portion has an elastic region,
that the elastic region is provided in at least a part of a region on the one side relative to a lateral center of the crotch portion, and
that the elastic region is capable of stretching and contracting in the lateral direction.

According to this absorbent article, the target region is pulled laterally outward (to the one side) by the contractive force exhibited by the elastic region. In other words, force in the shearing direction is generated at the faces where the target region and the fastening portion are engaged. Accordingly, hooks of the fastening portion and loops of the target region firmly mesh together, making it difficult to come apart. This makes it possible to more firmly fasten the fastening portion to the target region.

In the above absorbent article, it is desirable that the elastic region provided in the front waist portion does not exert on the target region a force for causing the target region to contract in the lateral direction.

According to this absorbent article, it is possible to suppress the case where the target region itself contracts in the lateral direction. This makes the target region easier to keep flat, and makes the fastening portion easier to be fastened.

In the above absorbent article, it is desirable
that an elastic region is provided in at least a part of the back waist portion, and
that the elastic region is capable of stretching and contracting in the lateral direction.

According to this absorbent article, the fastening portion is pulled laterally outward (to the other side) by the contractive force exhibited by the elastic region. In other words, force in the shearing direction is generated at the faces where the target region and the fastening portion are engaged. Accordingly, hooks of the fastening portion and loops of the target region firmly mesh together, making it difficult to come apart. This makes it possible to more firmly fasten the fastening portion to the target region.

In the above absorbent article, it is desirable that the elastic region provided in the back waist portion does not exert on the fastening portion a force for causing the fastening portion to contract in the lateral direction.

According to this absorbent article, it is possible to suppress the case where the fastening portion itself contracts in the lateral direction. This makes the fastening portion easier to keep flat and to be engaged with the target region.

In the above absorbent article, it is desirable that a longitudinal length of the fastening portion is shorter than a longitudinal length of the first joining portion.

According to this absorbent article, in the front waist portion, stretching force generated by the elastic region is likely to exert in the longitudinal range in which the first joining portion is formed. Accordingly, arranging the fastening portion in this range makes it possible to exert the stretching force generated by the elastic region on the entire longitudinal region of the fastening portion. This makes force in the shearing direction be effectively exerted on the target region and the fastening portion, and these members can be more firmly engaged with each other.

In the above absorbent article, it is desirable
that a leg-gather elastic member is provided in each of two lateral end portions of the crotch portion, that the leg-gather elastic member is capable of stretching and contracting in the longitudinal direction, and that a longitudinal range on which the leg-gather elastic member exerts its elastic force does not overlap with the fastening portion.

According to this absorbent article, stretching force in the longitudinal direction generated by the leg-gather elastic members is not exerted on the target region, suppressing the case where the target region is pulled longitudinally and distorted. This makes it easier for the target region to keep flat. This makes it possible to more easily fasten the fastening portion to the target region.

Embodiments

Basic Configuration of Disposable Diaper 1

Figure 2:
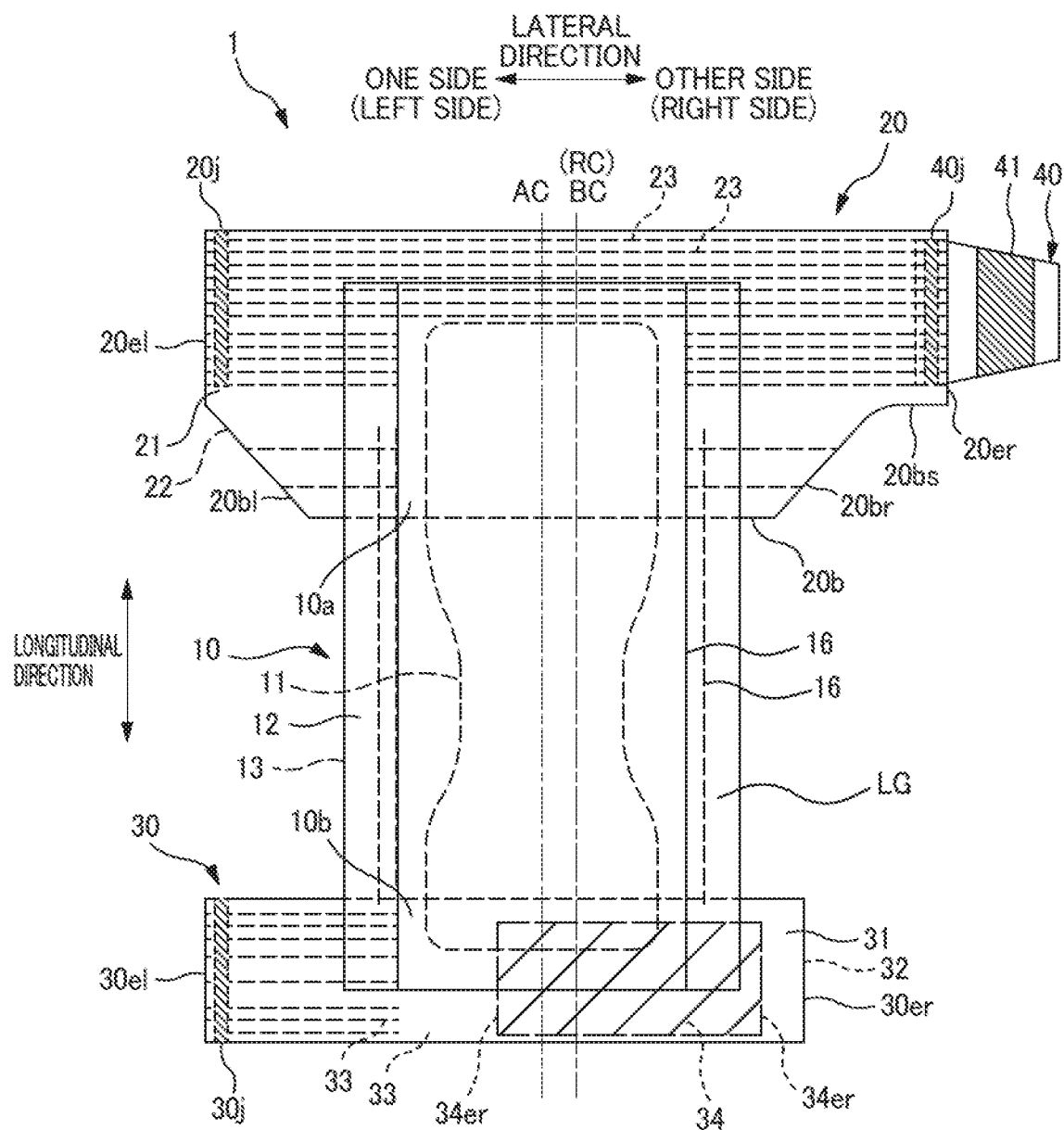
FIG. 2 is a plan view of the diaper 1 in an unfolded state.
Figure 3:
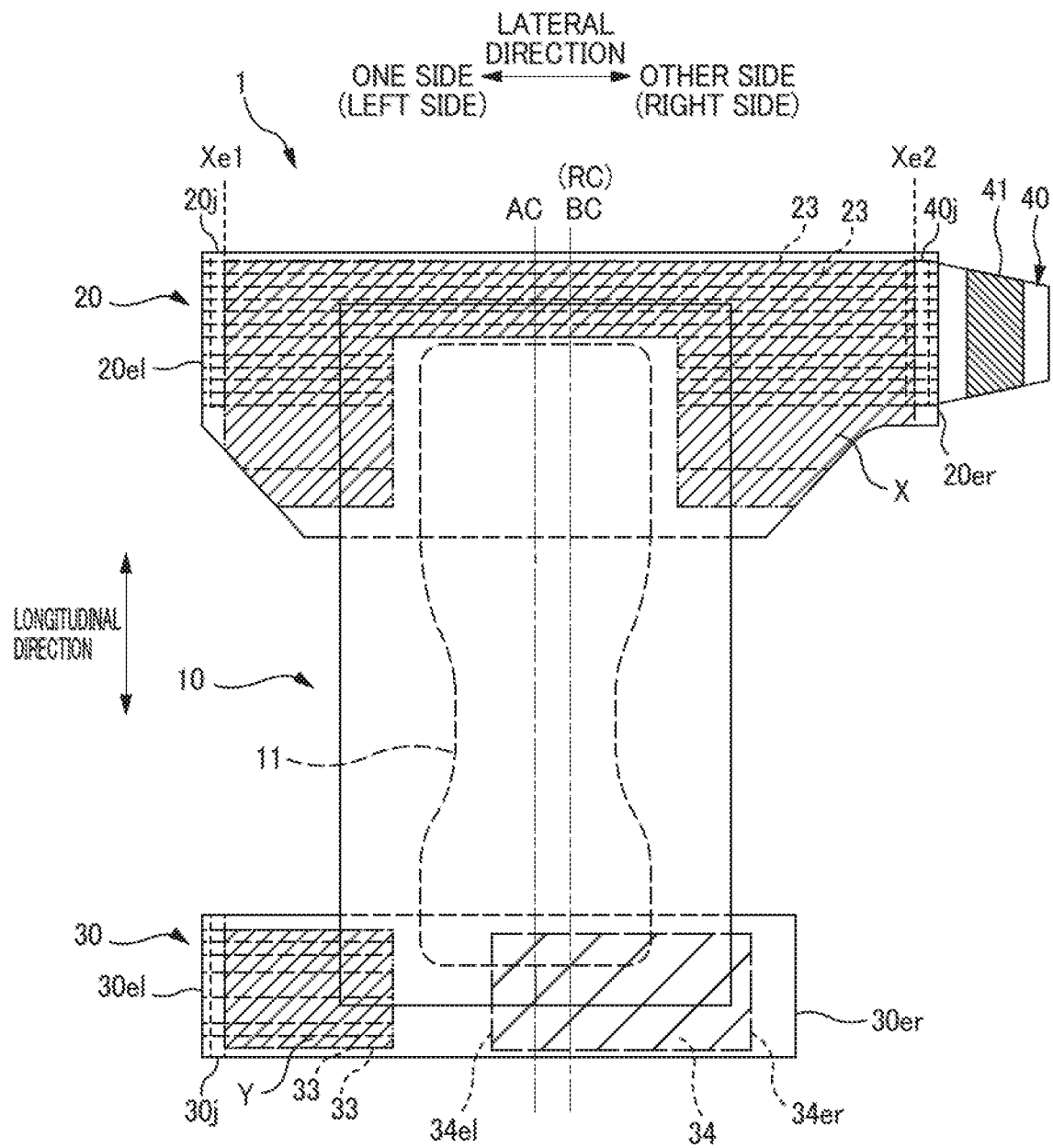
FIG. 3 is a diagram illustrating elastic regions X and Y.

The following describes the configuration of a half-open disposable diaper 1 (hereinafter, also simply called the diaper 1) as an example of an absorbent article according to the present embodiment. FIG. 1 is a schematic perspective view of the diaper 1 according to the present embodiment. FIG. 2 is a plan view of the diaper 1 in an unfolded state. The unfolded state is a state where a fastening portion 41 of the diaper 1 in FIG. 1 is detached from a target region 34, a first joining portion 1b is uncoupled and opened, and the entirety of the diaper 1 is laid flat. FIG. 3 is a diagram illustrating elastic regions X and Y.

The diaper 1 according to the present embodiment is a disposable diaper that is to be worn by mainly a newborn infant, an infant, or the like. As shown in FIG. 1, the diaper 1 has a "longitudinal direction", a "lateral direction" that intersects the longitudinal direction, and a "front-back direction" that intersects the longitudinal direction and the lateral direction. Also, in the following description, the left side in the lateral direction is the "one side", and the right side is the "other side" (see FIGS. 1 and 2).

The diaper 1 includes: an absorbent main body 10 (also called a "crotch portion") that is arranged at the crotch of the wearer and absorbs excrement; a back waist portion 20 that covers the back side of the wearer; and a front waist portion 30 and a fastening member 40 that cover the stomach side of the wearer. The diaper 1 in the unfolded state shown in FIG. 2 is folded in half with an approximately central position in the longitudinal direction serving as the folding position, and end portions of the back waist portion 20 and the front waist portion 30 on one side in the lateral direction are joined together in the first joining portion 1b, thus forming a leg opening 1HL on one side. The end portions of the back waist portion 20 and the front waist portion 30 on the other side in the lateral direction are not joined together, and a leg opening 1HL on the other side and a waist opening 1HB are formed by fastening the fastening member 40 to the front waist portion 30. In other words, the diaper 1 of the present embodiment is a so-called "half-open diaper" in which the back waist portion 20 and the front waist portion 30 are joined and closed on the one side in the lateral direction, and are unjoined and open on the other side.

The back waist portion 20 and the front waist portion 30 have an approximately rectangular planar shape, and in the unfolded state in FIG. 2, the back waist portion 20 and the front waist portion 30 are parallel with a space between each other in the longitudinal direction, and are bridged by the absorbent main body 10. Also, the back waist portion 20 is fixed to one end portion 10a of the absorbent main body 10, and the front waist portion 30 is fixed to an other end portion 10b.

Absorbent Main Body 10

The absorbent main body 10 (crotch portion) is approximately shaped as an elongated rectangle in a plan view, and is arranged at a central position in the lateral direction, with its lengthwise direction extending along the longitudinal direction of the diaper 1. In FIG. 2, a center line AC is the center of the absorbent main body 10 in the lateral direction. The absorbent main body 10 includes: an absorbent body 11 that absorbs and holds a liquid; a liquid-permeable top face sheet 12 that covers the absorbent body 11 on the wearer's skin side and allows the passage of excrement such as urine; and a liquid-impermeable back-face sheet 13 that covers the absorbent body 11 on the non-skin side and prevents the leakage of a liquid from the non-skin side. The absorbent body 11 is constituted by liquid-absorbent fibers such as pulp fibers and is formed with a predetermined shape such as approximately an hourglass shape in a plan view as shown in FIG. 2, and has a superabsorbent polymer incorporated therein.

Also, leg gathers LG (leg elastic portions) that stretch and contract along the longitudinal direction are provided at locations on respective side portions in the lateral direction of the absorbent main body 10. The leg gathers LG are formed by a nonwoven fabric or the like, and each include a leg-gather elastic member 16 that stretches and contracts along the longitudinal direction. The leg-gather elastic members 16 are formed by an elastic string or the like, and are joined to the leg gathers LG with being stretched in the longitudinal direction, giving the leg gathers LG stretchability in the longitudinal direction. Also, a pair of leg side gathers LSG (barrier cuffs) may be further provided inward of the leg gathers LG in the lateral direction of the absorbent main body 10 (not shown in FIG. 2).

Back Waist Portion 20

The back waist portion 20 includes: a skin-side member 21 that is located on the wearer's skin side; a non-skin-side member 22 that is located on the non-skin side; and multiple elastic strings 23 that are located between the skin-side member 21 and the non-skin-side member 22. The skin-side member 21 and the non-skin-side member 22 are each a flexible sheet member that is constituted by a nonwoven fabric or the like. The elastic strings 23 are elastic members that give the back waist portion 20 stretchability in the lateral direction. In the present embodiment, the elastic strings 23 are arranged side-by-side at a predetermined longitudinal interval. And the elastic strings 23 are joined with an adhesive between the skin-side member 21 and the non-skin-side member 22 with being stretched in the lateral direction.

In FIG. 2, a center line RC indicates the lateral center of the back waist portion 20. A joining region 20j is provided in an end portion on the one side of the back waist portion 20. The joining region 20j is joined to a joining region 30j (described later) of the front waist portion 30 by a predetermined joining means (e.g., heat welding), forming a first joining portion 1b of the diaper 1. Also, a fixing region 40j is provided in an end portion on the other side of the back waist portion 20. The fastening member 40 is fixed to the fixing region 40j.

The elastic strings 23 form an elastic region X and improve the fit of the diaper 1. In the upper end portion of the back waist portion 20, the elastic strings 23 are continuous from the one end side to the other end side in the lateral direction, and are arranged side-by-side at a predetermined longitudinal interval. Here, in the longitudinal central portion and the lower longitudinal end portion of the back waist portion 20, the back waist portion 20 is overlapped with the absorbent body 11. In that region, in the widthwise central portion of the back waist portion 20, in which the absorbent body 11 is provided, the elastic strings 23 are not provided. On the other hand, in the respective regions to the left and right of the absorbent body 11, the elastic strings 23 are provided substantially parallel with each other.

As shown in FIG. 3, the elastic region X is the region where the elastic strings 23 are provided, and extends from the laterally inward end (the end on the other side) of the joining region 20j to the laterally inward end (the end on the one side) of the fixing region 40j; as mentioned above, in the lateral direction, the joining region 20j is provided on the one side of the back waist portion 20, and the fixing region 40j is provided on the other side. In FIG. 3, the elastic region X is indicated by the hatched portion. Note that for convenience in FIG. 3, hatching has been omitted for the joining regions 20j and 30j and the fixing region 40j. As shown in FIGS. 2 and 3, the elastic strings 23 extend to lateral ends 20er and 20el of the back waist portion 20. But, providing the joining region 20j and the fixing region 40j respectively in these lateral end portions of the back waist portion 20 makes it substantially impossible to exhibit stretching force of the following regions: the joining region 20j; the portion laterally outward of the joining region 20j; the fixing region 40j; and the portion laterally outward of the fixing region 40j. A one-side end Xe1 of the elastic region X is at the same position as the laterally inward end of the joining region 20j, and an other-side end Xe2 of the elastic region X is at the same position as the laterally inward end of the fixing region 40j. Note that a configuration is possible in which the elastic strings 23 are also provided in a region other than the elastic region X indicated by the hatched portion in FIG. 3 (a non-elastic region), and the elastic strings 23 are cut in this non-elastic region to prevent stretchability from being exhibited.

A center line BC indicates the approximate center of the body of a wearer when a wearer's leg has been inserted. In the present embodiment, the center line BC is at the same position as the center line RC that indicates the lateral center of the back waist portion 20. The center line RC and the center line BC are located different from the center line AC that indicates the center of the absorbent main body 10, and are to the right (on the other side) of the center line AC. The reason for this will be described later.

In the back waist portion 20, on the one side of its lower end 20b, provided is an inclined portion 20b1 that is inclined toward the one-side end portion. On the other side of the lower end 20b, a straight portion 20bs and an inclined portion 20br are provided; the straight portion 20bs is substantially parallel with the lower end of the front waist portion 30, and the inclined portion 20br is on the laterally inward side of the straight portion 20bs and is symmetrical with the inclined portion 20b1 about the center line AC. Due to the straight portion 20bs being substantially parallel with the lower end of the front waist portion 30, when the diaper 1 is worn by fastening the fastening portion 41 to the target region 34, the lower end of the front waist portion 30 can be aligned with the straight portion 20bs of the back waist portion 20. This improves the appearance of the diaper 1 when it is worn.

Fastening Member 40

The fastening member 40 is a tape substrate having a substantially trapezoidal shape, and is fixed to the back waist portion 20 in the fixing region 40j using a predetermined fixing means such as heat welding. The fastening member 40 has a fastening portion 41, which is a hook-and-loop fastener having a plurality of fastening projections (hooks) on its skin-side surface. The fastening projections of the fastening portion 41 are hooked to the target region 34 provided in the front waist portion 30, fastening the fastening member 40 to the front waist portion 30. The leg opening 1HL on the other side, and the waist opening 1HB are thus formed (see FIG. 1).

Note that in the example shown in FIG. 2, the back waist portion 20 and the fastening member 40 are formed as separate members, and are joined to each other in the fixing region 40j. But, the back waist portion 20 and the fastening member 40 may be formed together as a single unit. Specifically, the front waist portion 30 and the fastening member 40 in FIG. 2 may be combined into the "back waist portion 20". In this case, the fastening portion 41 is directly joined to the laterally, other-side end portion of the back waist portion 20. In this case, the elastic region X is provided such that the other-side end Xe2 of the elastic region X is located inside (laterally closer to the one side than) the laterally, one-side end portion of the fastening portion 41.

Front Waist Portion 30

The front waist portion 30 includes: a skin-side member 31 that is located on the wearer's skin side; a non-skin-side member 32 that is located on the non-skin side; a plurality of elastic strings 33 (elastic members) that are located between the skin-side member 31 and the non-skin-side member 32; and the target region 34 on the non-skin-side surface of the front waist portion 30. The skin-side member 31 and the non-skin-side member 32 are each a flexible sheet member that is constituted by a nonwoven fabric or the like. The elastic strings 33 are elastic members that give the front waist portion 30 lateral stretchability. In the present embodiment, the elastic strings 33 are arranged side-by-side at a predetermined longitudinal interval. And, the elastic strings 33 are joined with an adhesive between the skin-side member 31 and the non-skin-side member 32 with being stretched in the lateral direction. The target region 34 is a region capable of engaging with the fastening portion 41. For example, the target region 34 is made of a member whose fibers on the upper surface of a nonwoven fabric are formed into loop shapes so as to be readily engaged with the fastening projections (hooks) of the fastening portion 41. Note that the following configuration is also acceptable: instead of making the target region 34 and the front waist portion 30 different, the target region 34 is formed by processing a partial region of the non-skin-side member 32 of the front waist portion 30.

The elastic strings 33 form an elastic region Y, improving the fit of the diaper 1. The elastic strings 33 extend from a laterally, one-side (left) end 30el of the front waist portion 30 to a predetermined lateral position that is located on the one side relative to the center line AC. In the present embodiment, the elastic strings 33 (the elastic region Y) are provided in a range extending from the lateral end 30el to a position that is located on the one side (left) relative to a laterally, one-side end 34el of the target region 34, this range not being overlapped with the absorbent body 11. In contrast, the elastic strings 33 are not provided in the range from a laterally, other-side (right) end 30er to the center line AC. Also, as shown by a hatched portion in FIG. 3, the elastic region Y is a region in which the elastic strings 33 are provided from the laterally inward end of the joining region 30j to a position that is located on the one side (left) relative to the end 34el.

Note that a configuration is possible in which the elastic strings 33 are also provided in a region other than the elastic region Y indicated by the hatched portion in FIG. 3 (a non-elastic region), and the elastic strings 33 are cut in this non-elastic region to prevent stretchability from being exhibited.

As shown in FIG. 2, the joining region 30*j* is provided in the left end portion of the front waist portion 30. The joining region 30*j* is joined with the joining region 20*j* of the back waist portion 20, forming the first joining portion 1*b*. Also, the lateral length of the front waist portion 30 is shorter than the lateral length of the back waist portion 20. Specifically, in the lateral direction, the one-side (left) end 30*el* of the front waist portion 30 is provided at substantially the same position as the one-side (left) end 20*el* of the back waist portion 20. In contrast, in the lateral direction, the other-side (right) end 30*er* of the front waist portion 30 is provided inside the other-side (right) end 20*er* of the back waist portion 20.

Method of Putting on Diaper 1

Figure 4:
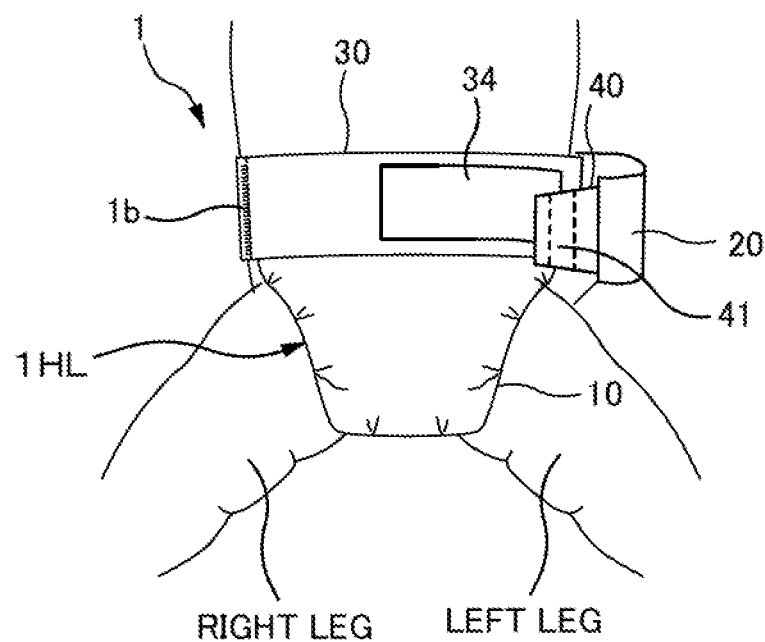
FIG. 4 is a diagram illustrating a method of putting on the diaper 1.

FIG. 4 is a diagram illustrating a method of putting on the diaper 1. As described above, in the laterally one-side end portion of the diaper 1, the front waist portion 30 and the back waist portion 20 are joined together by the first joining portion 1*b*, thus forming the leg opening 1HL. In contrast, the laterally, other-side end portion is in an open state in which the front waist portion 30 and the back waist portion 20 are not joined together. In other words, the diaper 1 is in a state where its lateral one side is open. When this diaper 1 is to be put on the wearer (an infant or the like), first, one leg (the right leg) of the wearer is inserted into the leg opening 1HL formed on the one side in the lateral direction of the diaper 1. Then, the leg opening 1HL on the one side is arranged at the joint of the right leg of the wearer, that is to say at the same position as the one leg in the worn state. Thereafter, the operator putting on the diaper on pulls the other-side end portion of the front waist portion 30 toward laterally the other side by his/her hand, and then holds it in that state. The operator then pulls the fastening member 40 (the other-side end portion of the back waist portion 20) toward laterally the other side by his/her other hand, and wraps it around to the front side of the front waist portion 30. Then, the operator fastens the fastening portion 41 to the target region 34 of the front waist portion 30. Thus, the leg opening on the other side is formed, putting the diaper 1 on the wearer.

With this putting-on method, the fastening portion 41 is fastened to the target region 34 while the one of the wearer's legs has been inserted through the leg opening 1HL on the one side, thus making it possible to form the leg opening 1HL on the other side and the waist opening 1HB at the same time. This makes it possible to put on the diaper 1 easily even if the wearer (a newborn infant or an infant) is wriggling their legs.

In this method of putting on the diaper 1, the back waist portion 20 (the fastening member 40) and the front waist portion 30 are pulled in the lateral direction, and therefore the position of the absorbent main body 10 joined to the waist portions 20 and 30 moves laterally toward the other side. In other words, the lateral center of the absorbent main body 10 shifts. For this reason, in the diaper 1, in the state where one of wearer's legs has been inserted into the leg opening 1HL on the lateral one side, the lateral center line RC of the back waist portion 20 is located on the other side relative to the lateral center line AC of the absorbent main body 10.

When one of wearer's legs has been inserted into the leg opening 1HL, the center line AC of the absorbent main body 10 is located on the one side (the right leg side) of the center line BC that indicates the center of the body of the wearer.

In this state, the fastening member 40 is pulled to the other side, and the fastening portion 41 is fastened to the front waist portion 30, forming the diaper 1 into a shape when it is worn. Then, the back waist portion 20 stretches in the lateral direction, and the absorbent main body 10 moves to the other side (the left leg side). Accordingly, the center line AC and the center line BC approach each other, and the absorbent main body 10 can be brought near the center of the body of the wearer.

Arrangement of Target Region

As illustrated in FIG. 4, when the diaper 1 according to the present embodiment is put on the wearer, the waist opening and leg openings of the diaper 1 are fitted to the wearer's body by fastening the fastening portion 41 to the target region 34 of the front waist portion 30. Accordingly, in order to achieve a favorable fit, it is desirable that the region of the fastening portion 41 that can be fastened to the target region 34 is increased in size, and that the size of the waist opening 1HB can be adjusted a large amount. In particular, envisioning that the wearer of the diaper 1 is a newborn infant or an infant, it is desirable that the size of the waist opening 1HB can be freely adjusted due to the fact that, for example, the waist size of an infant changes a large amount before and after breast-feeding.

However, with the half-open diaper disclosed in the foregoing PTL 1, the target region (adhesive region 8 in PTL 1) is provided in only the laterally one-side region of the front waist portion, and it has been difficult to adjust the fastening position a sufficiently large amount. This is because the half-open diaper employs, as-is, the structure of a conventional fully-open diaper, that is to say a diaper in which the two lateral ends of the front and back waist members are not joined together, and in which fastening portions provided on the two lateral ends are fastened on the stomach side to put on the diaper. In conventional fully-open diapers, the right fastening portion is fastened to the right target region, and the left fastening portion is fastened to the left target region, and it is not possible to fasten the left-side fastening portion to the right-side target region. For this reason, in the half-open diaper of PTL 1 as well, the target region for fastening the fastening portion on the one side (the right side) is provided on only the one side (the right side), and the region for fastening is small.

In view of this, in the diaper 1 of the present embodiment, the target region 34 is provided over a larger range in the front waist portion 30, thus making it possible to enable wider adjustment of the fastening position of the fastening portion 41 and also realize a favorable fit. The following is a detailed description of the arrangement of the target region 34.

Figure 5:
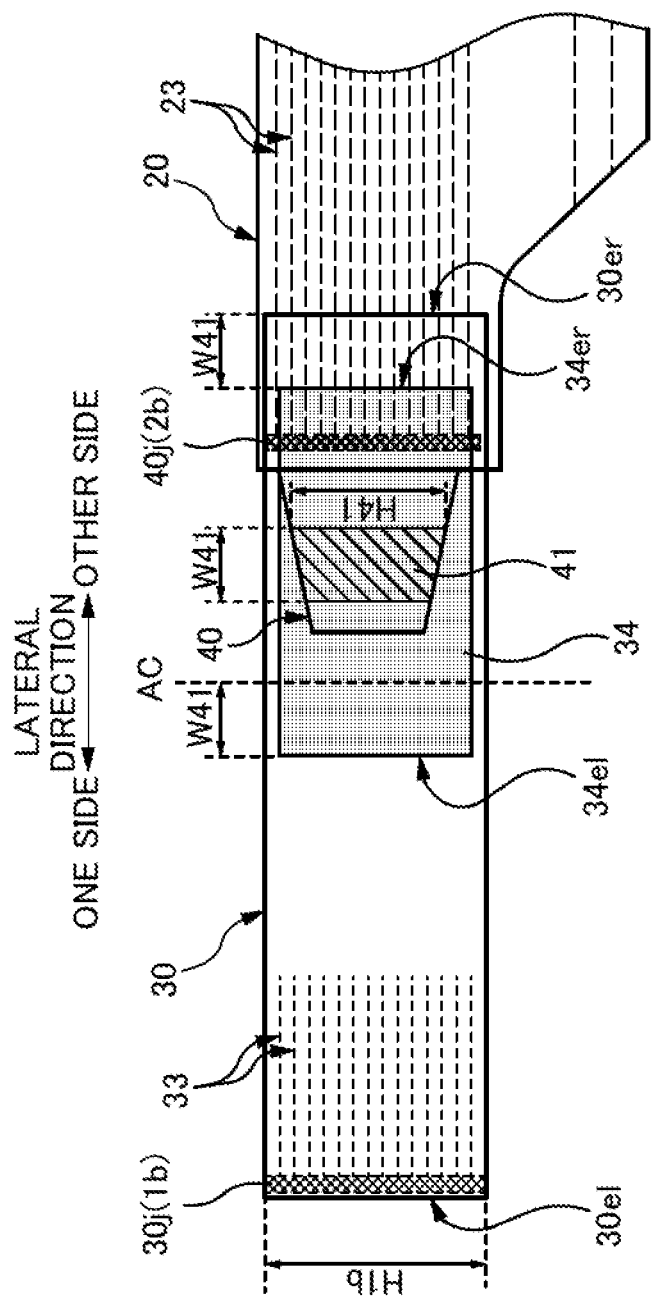
FIG. 5 is a diagram illustrating a positional relationship between a target region 34 and a fastening portion 41 of the diaper 1 when they are fastened.

FIG. 5 is a diagram illustrating the positional relationship between the target region 34 and the fastening portion 41 of the diaper 1 when they are fastened. FIG. 5 shows a front view of the state where the back waist portion 20 is overlaid on the front side (non-skin side) of the front waist portion 30, and the fastening portion 41 is fastened to the target region 34. Note that for the sake of convenience in the description, the back waist portion 20 (the fastening member 40) is shown in a transparent manner from the non-skin side in FIG. 5 in order to make the front waist portion 30 visible. The target region 34 provided on the front waist portion 30 is indicated by a shaded portion, and the fastening portion 41 is indicated by a hatched portion. The end 34*el* is in the end of the target region 34 on the one side in the lateral direction, the end 34*er* is the end on the other side, and the length (width) of the fastening portion 41 in the lateral direction is indicated by a width W41. As shown in FIG. 5, the fastening portion 41 and the target region 34 are fastened with each other in the region in which they are overlapped.

In the diaper 1, the one-side lateral end 34el of the target region 34 is provided at a lateral position located on the one side (the left side) relative to the central position (the center line AC) of the absorbent main body 10 (the crotch portion). Specifically, the lateral end 34el is provided between the center line AC and the position on the one side away from the center line AC a distance corresponding to the width W41. In other words, at least a portion of the target region 34 is provided on the one side of the center line AC. Accordingly, the fastening portion 41 can be fastened so as to obtain a smaller waist opening 1HB. Note that FIG. 5 shows the case where the lateral end 34el is provided at the position on the one side away from the center line AC a distance corresponding to the width W41, and the target region 34 has been expanded the most to the one side.

Figure 6:
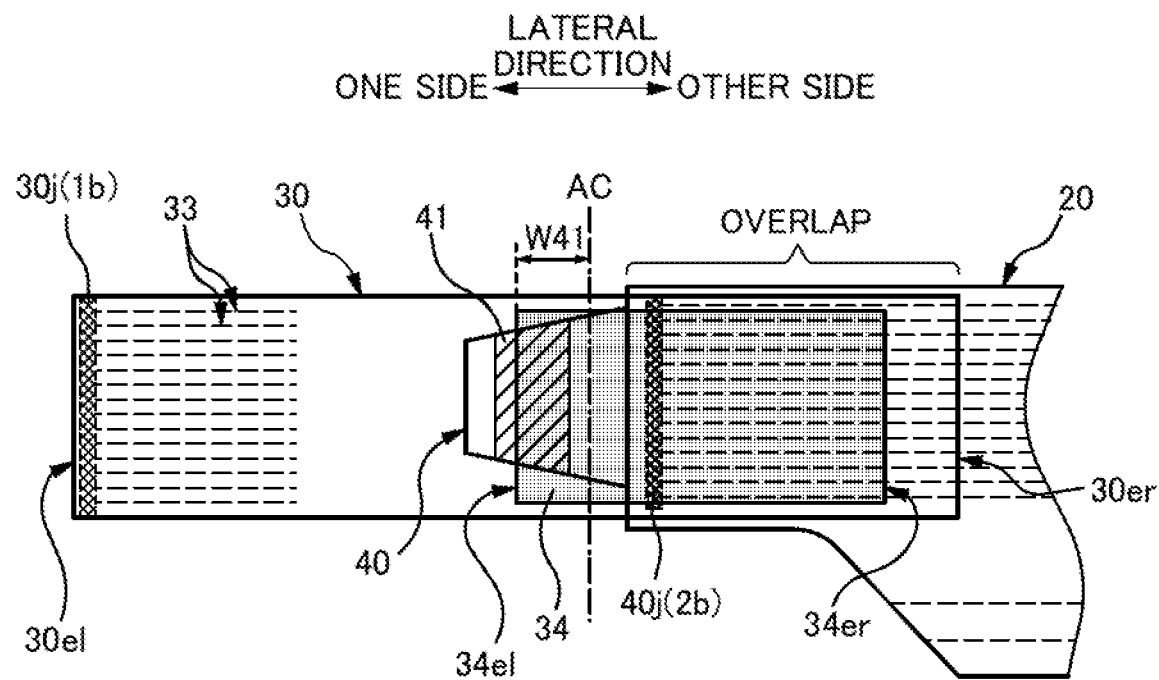
FIG. 6 is a diagram showing a state where the fastening portion 41 is fastened to obtain a smaller waist opening 1HB than in the case shown in FIG. 5.

FIG. 6 is a diagram showing a state where the fastening portion 41 is fastened to obtain a smaller waist opening 1HB than in the case shown in FIG. 5. Due to the target region 34 being provided in a region on the one side relative to the center line AC, the fastening portion 41 can be fastened at a position located on the one side relative to the center line AC. This increases in size the overlapping portions of the back waist portion 20 and the front waist portion 30, reducing the size of the waist opening 1HB correspondingly. This makes it possible to provide a favorable fit for a wearer whose waist size is small (e.g., an infant). When fastening the fastening portion 41, it is not necessarily required that the entire region of the fastening portion 41 is overlapped with the target region 34. It is sufficient that the regions are at least partially overlapped as shown in FIG. 6. It should be noted that the engagement between the fastening portion 41 and the target region 34 becomes stronger as the area of the overlapping portions between them increases in size. Accordingly, it is desirable that the entire region of the fastening portion 41 is overlapped with the target region 34.

Figure 7:
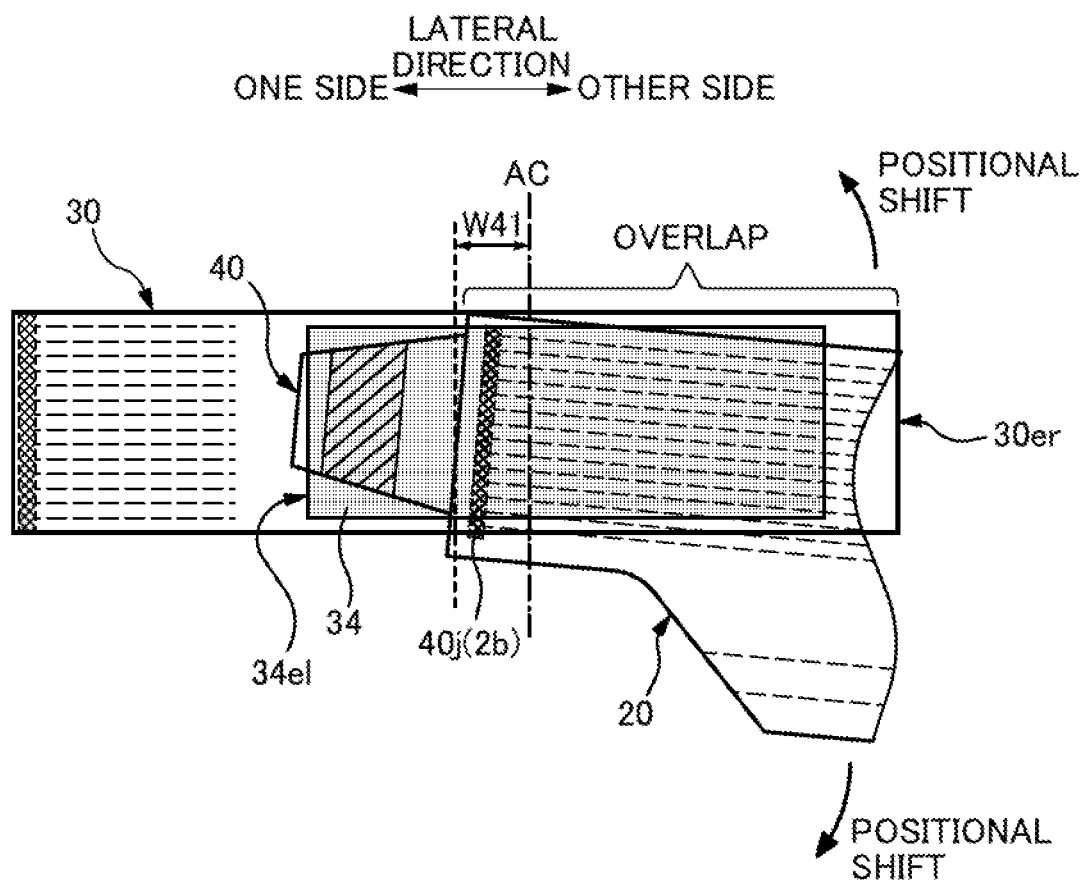
FIG. 7 is a diagram showing an example of a case where the target region 34 is expanded to one side in the lateral direction compared to the state shown in FIG. 5.

On the other hand, if the fastening portion 41 can be fastened to the target region 34 at a position that is located on the one side excessively far away from the center line AC, this makes it more likely to shift the position of the diaper 1 when the diaper 1 being worn. FIG. 7 is a diagram showing an example of a case where the target region 34 is expanded to one side in the lateral direction compared to the state shown in FIG. 5. In this case, the fastening portion 41 can be fastened at a position that is located on the one side largely far away from the center line AC (to a position that is located away a distance greater than W41), and the overlapping portions of the back waist portion 20 and the front waist portion 30 increase in size. In these overlapping portions, the back waist portion 20 and the front waist portion 30 are fastened by only the fastening portion 41, and the other regions are not fixed. Accordingly, if the wearer of the diaper 1 moves their body, there is a risk of unfixed overlapping portions becoming misaligned with each other with the fastening portion 41 serving as the fulcrum, as shown in FIG. 7. The influence of this misalignment increases the larger the lateral distance from the fastening portion 41 to the other-side end 30er of the front waist portion 30 is. In other words, the larger the overlapping portions of the back waist portion 20 and the front waist portion 30 are, the more freely the end 30er moves, and the more likely the position of the diaper 1 is to become shifted.

In view of this, in the present embodiment, the end 34el of the target region 34 is located inside the position on the one side away from the center line AC a distance corresponding to the width W41. Thus, the region to which the fastening portion 41 can be fastened is restricted from being excessively expanded to the one side. Accordingly, it is possible to ensure on the one side a wide range for fastening the fastening portion 41 while suppressing excessive increase of the area of the overlapping portions of the back waist portion 20 and the front waist portion 30. This makes it possible to improve the fit of the diaper 1 when it is put on, and to make it unlikely for positional shift to occur.

Also, in the diaper 1, the other-side lateral end 34er of the target region 34 is provided between the center line AC and the position on the one side away from the other-side lateral end 30er of the front waist portion 30 a distance corresponding to the width W41. Accordingly, the fastening portion 41 can be fastened so as to obtain a larger waist opening 1HB. Note that FIG. 5 shows the case where the lateral end 34er is provided at the position on the one side away from the other-side lateral end 30er a distance corresponding to the width W41, and the target region 41 has been expanded the most to the other side.

Figure 8:
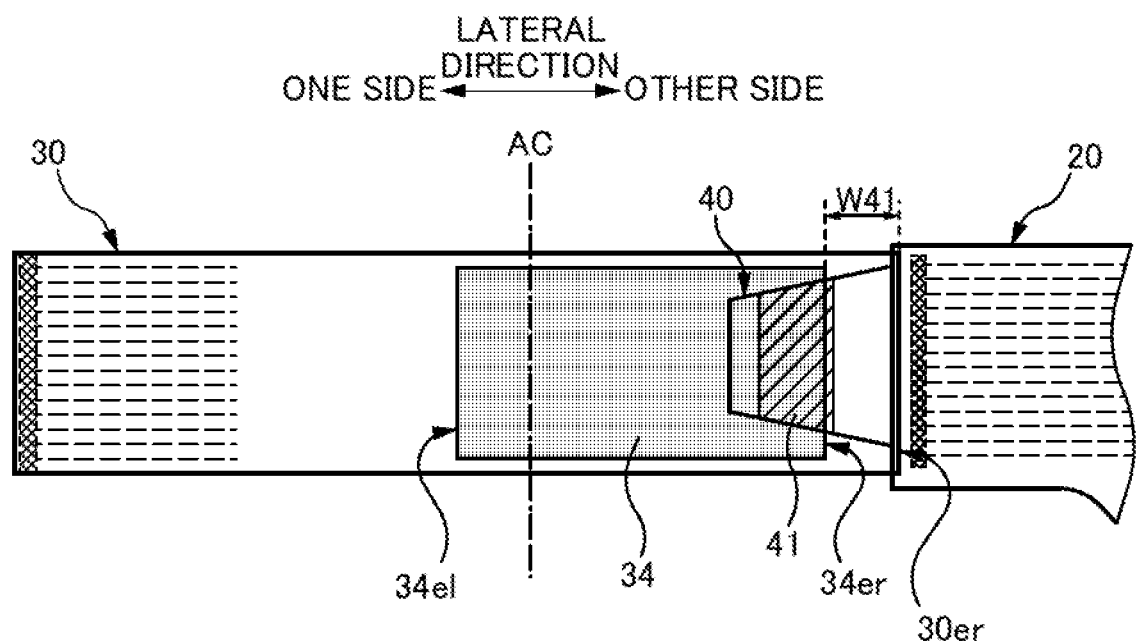
FIG. 8 is a diagram showing a state where the fastening portion 41 is fastened to obtain a larger waist opening 1HB than in the case shown in FIG. 5.

FIG. 8 is a diagram showing a state where the fastening portion 41 is fastened to obtain a larger waist opening 1HB than in the case shown in FIG. 5. In FIG. 8, the overlapping portions of the back waist portion 20 and the front waist portion 30 are very small, enlarging the side of the waist opening 1HB correspondingly. This makes it possible to provide favorable fit for a wearer whose waist size is large.

Figure 9:
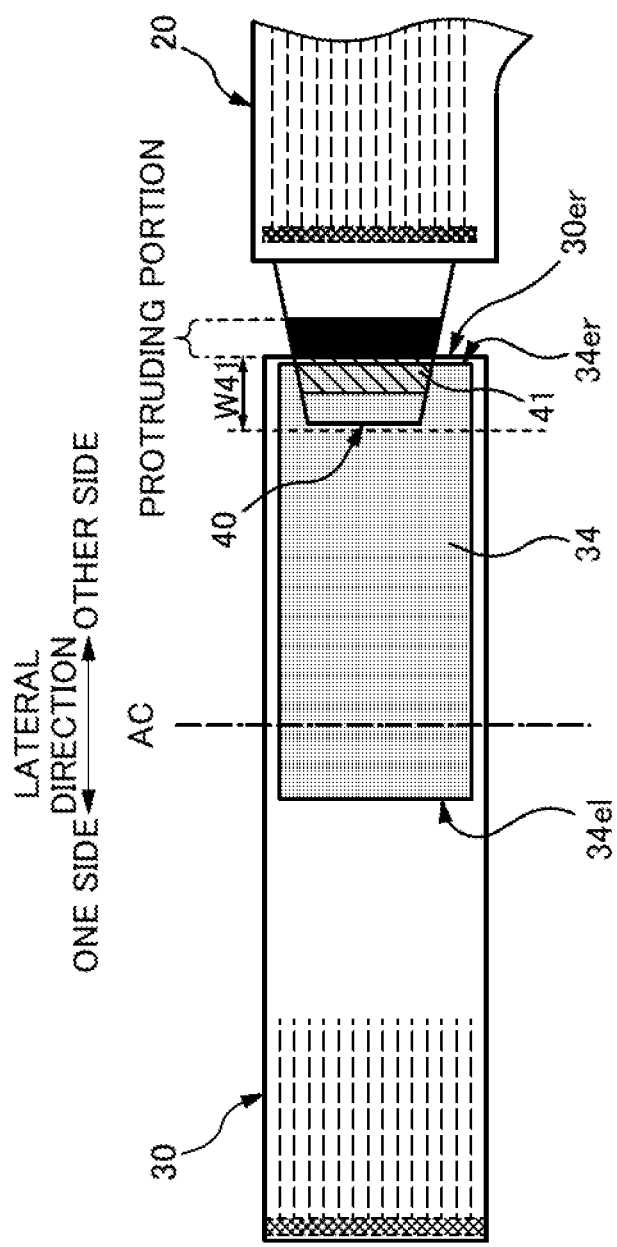
FIG. 9 is a diagram showing an example of a case where the target region 34 is expanded to the other side in the lateral direction compared to the state shown in FIG. 5.

The reason that the end 34er is located away from the lateral other-side end 30er of the front waist portion 30 a distance corresponding to the width W41 is for making it less likely to cause discomfort to the wearer when the diaper 1 is worn. FIG. 9 is a diagram showing an example of the case where the target region 34 is expanded to the other side in the lateral direction compared to the state shown in FIG. 5. In FIG. 9, the target region 34 is expanded to the other side in the lateral direction, and the other-side end 34er of the target region 34 is provided in the vicinity of the lateral other-side end 30er of the front waist portion 30. If the fastening portion 41 is fastened to the target region 34 in this state, there are cases where a portion of the fastening portion 41 protrudes to the other side beyond the lateral other-side end 30er of the front waist portion 30 as shown by the solid black portion in FIG. 9. The portion of the fastening portion 41 that protrudes from the end 30er to the other side (the solid black portion in FIG. 9) comes into direct contact with the wearer's skin, and thus there is a risk of causing discomfort to the wearer. In particular, infants and the like have delicate skin, and therefore direct contact with the skin-side surface of the fastening portion 41 (the hook-and-loop fastener) has a risk of damaging the skin.

In view of this, in the present embodiment, the end 34er of the target region 34 is located on the one side away from the end 30er of the front waist portion 30 a distance corresponding to the width W41, and therefore when the fastening portion 41 is fastened to the target region 34, the fastening portion 41 does not protrude from the end 30er of the front waist portion 30. This makes it possible to expand, to the other side, the range that the fastening portion 41 can be fastened to, suppressing the case of causing discomfort to the wearer.

Figure 10:
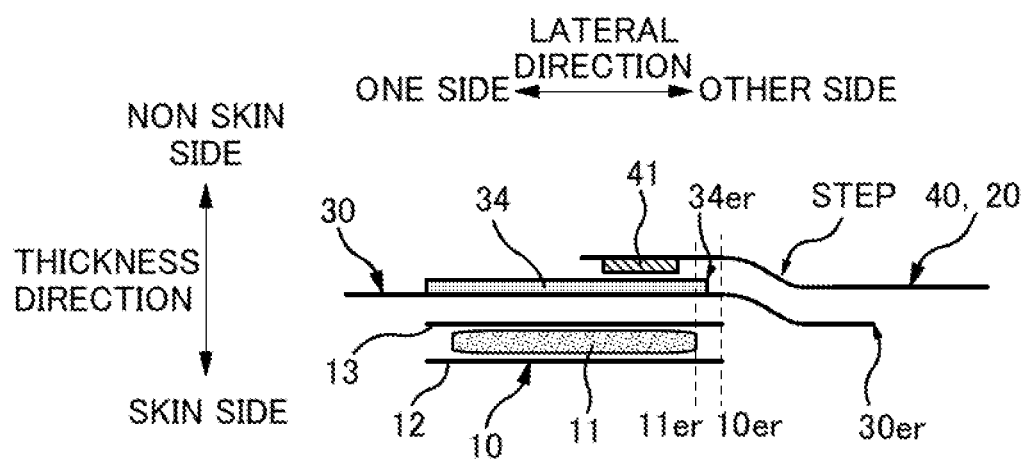
FIG. 10 is a schematic cross-sectional view taken along the thickness direction for illustrating a state where the fastening portion 41 and the target region 34 are fastened.

Note that the lateral other-side end 34er of the target region 34 may be located at a position that is laterally inside the lateral other-side end 10er of the absorbent main body 10. FIG. 10 is a schematic cross-sectional view taken along the thickness direction for illustrating a state where the fastening portion 41 and the target region 34 are fastened. In the portion where the fastening portion 41 and the target region 34 are fastened, the absorbent main body 10, the front waist portion 30 (the target region 34), and the back waist portion 20 (the fastening member 40) are overlapped from the skin side to the non-skin side in the thickness direction. The absorbent main body 10 has the absorbent body 11, and thus is thicker than the front waist portion 30 and the back waist portion 20. For this reason, there are cases where, as shown in FIG. 10, the front waist portion 30 has a step between the portion overlapped with the absorbent main body 10 (on the one side relative to the end 10e) and the portion that is not overlapped (on the other side relative to the end 10er). If the target region 34 is provided in this stepped portion, there is a risk that the target region 34 will not be kept being flat due to the influence of the stepped portion, and that the fastening portion 41 will not be fastened firmly.

In contrast, if the target region 34 is provided in the region on the one side relative to the end 10er, the target region 34 is likely to have a flat shape, and the fastening portion 41 is easily fastened. Also, such a region located on the one side relative to the end 10er is stiffer due to the overlapping of the members that constitute the absorbent main body 10 (the absorbent body 11, the top face sheet 12, and the back-face sheet 13). Accordingly, the target region 34 is likely to be more stably kept in a flat state, making it easier to fasten the fastening portion 41. Also, in this case, there is a greater distance between the other-side end 34er of the target region 34 and the lateral other-side end 30er of the front waist portion 30, and therefore there is a lower possibility of the fastening portion 41 being fastened protruding from the end 30er (see FIG. 9).

Note that the lateral other-side end 34er of the target region 34 may be located laterally inside the lateral other-side end 11er of the absorbent body 11. If the absorbent body 11 and the target region 34 are overlapped in the lateral direction, the target region 34 is less likely to be influenced by the step mentioned above, and is more likely to be kept being flat by the stiffer area.

Elastic Region

In the diaper 1, making the target region 34 wider in the lateral direction expands the range that the fastening portion 41 can be fastened to. This makes necessary the configuration in which the fastening portion 41 is firmly fastened to the target region 34 regardless of the fastening position. In other words, it is necessary to strengthen the engaging force of the fastening portion 41 with the target region 34.

Figure 11:
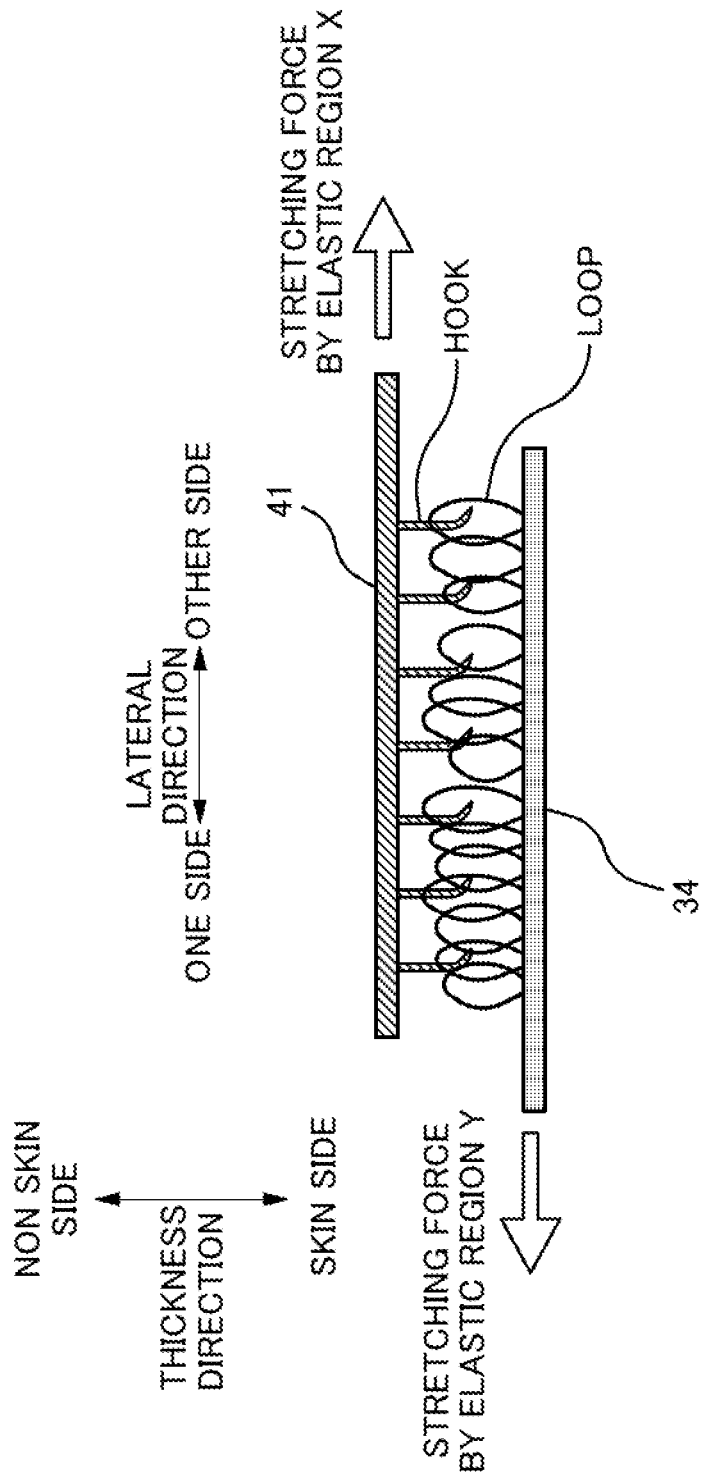
FIG. 11 is a diagram illustrating force that acts on the target region 34 and the fastening portion 41 when they are fastened.

In view of this, in the diaper 1 of the present embodiment, the engaging force of the fastening portion 41 is strengthened by appropriately providing the elastic regions X and Y. FIG. 11 is a diagram illustrating force that acts on the target region 34 and the fastening portion 41 when they are fastened. In FIG. 11, the states of the target region 34 and the fastening portion 41 are shown schematically in order to facilitate the description. As described above, multiple fastening projections (hooks) are provided on a surface of the fastening portion 41, and the fastening portion 41 is fastened to the target region 34 by the hooks becoming caught on the fibers (loops) at a surface of the target region 34.

In the front waist portion 30 of the diaper 1, the elastic region Y is provided in at least part of the region on the one side (left side) relative to the lateral center (center line AC) of the crotch portion. More specifically, the elastic region Y is provided on the one side relative to the lateral one-side end 34el of the target region 34. The elastic region Y exhibits lateral stretching force (lateral contractive force) by being stretched as the front waist portion 30 is pulled in the lateral direction when the diaper 1 is put on. Due to this stretching force, the target region 34 (the front waist portion 30) is pulled laterally to the one side, as shown in FIG. 11. In other words, force acts in a direction of causing shearing at the faces where the target region 34 and the fastening portion 41 are engaged. This makes the hooks of the fastening portion 41 less likely to be unhooked from the loops of the target region 34, and therefore these two members are strongly engaged with each other.

Similarly, the elastic region X is provided in at least part of the back waist portion 20 of the diaper 1. The elastic region X exhibits lateral stretching force (lateral contractive force) by being stretched as the back waist portion 20 is pulled in the lateral direction when the diaper 1 is put on. Due to this stretching force, the fastening portion 41 (the fastening member 40) is pulled laterally to the other side, as shown in FIG. 11. In other words, force acts in a direction of causing shearing at the faces where the target region 34 and the fastening portion 41 are engaged. This makes the hooks of the fastening portion 41 less likely to be unhooked from the loops of the target region 34, and therefore these two members are strongly engaged with each other.

Note that the elastic region Y and the target region 34 do not overlap in the front waist portion 30 (see FIG. 3), suppressing the case where the elastic region Y causes the target region 34 itself to contract in the lateral direction. In other words, force that the elastic region Y causes the target region 34 itself to contract is not applied to the target region 34. This makes the target region 34 easier to keep flat and to be engaged with the fastening portion 41.

Similarly, the elastic region X and the fastening portion 41 do not overlap in the back waist portion 20 (see FIG. 3), suppressing the case where the elastic region X causes the fastening portion 41 itself to contract in the lateral direction. In other words, force that the elastic region X causes the fastening portion 41 itself to contract is not applied to the fastening portion 41. This makes the fastening portion 41 easier to keep flat, and to be engaged with the target region 34.

Also, in the diaper 1 of the present embodiment, the maximum longitudinal length H41 of the fastening portion 41 is shorter than the longitudinal length H1b of the first joining portion 1b, in which the front waist portion 30 and the back waist portion 20 are joined together in the lateral one-side end portion (the longitudinal length of the joining region 30j of the front waist portion 30). As shown in FIG. 3, in the front waist portion 30, the elastic region Y is within the longitudinal range in which the joining region 30j (the first joining portion 1b) is formed. In other words, the elastic region Y exerts the stretching force within the longitudinal range in which the first joining portion 1b is formed. Accordingly, making the longitudinal length H41 of the fastening portion 41 shorter than the longitudinal length H1b of the first joining portion 1b enables the elastic region Y to exert its stretching force on the entire longitudinal region of the fastening portion 41 when fastening the fastening portion 41 and the target region 34. This makes force in the shearing direction (see FIG. 11) be effectively exerted on the target region 34 and the fastening portion 41, and these two members can be engaged more firmly.

Also, in the diaper 1, the region subjected to stretching force by the leg-gather elastic member 16 does not longitudinally overlap with the target region 34. Here, assume that the leg-gather elastic member 16 exerts its stretching force on the target region 34. In this case, there is a risk that by the target region 34 being pulled longitudinally (downward) causes a surface of the target region 34 to distort and to disturb the region 34 keeping flat. Thus, in this case, the fastening portion 41 is less likely to be fastened to the target region 34. In contrast, in the diaper 1 of the present embodiment, the stretching force generated by the leg-gather elastic member 16 is not exerted on the target region 34, suppressing the case where the target region 34 is pulled longitudinally and distorted. This makes it easier for the target region 34 to keep flat. This makes it possible to facilitate the fastening of the fastening portion 41 to the target region 34.

Note that in the above embodiment, the comparison of the lengths W41, H41, H1b, and the like shown in FIGS. 5 to 8 is made with stretching the absorbent main body 10, the back waist portion 20, and the front waist portion 30. This "stretching" state is a state where the absorbent main body 10 is stretched in the longitudinal direction without creases, and where the back waist portion 20 and the front waist portion 30 are stretched in the lateral direction without creases. More specifically, it is a state as follow: the absorbent main body is stretched in the longitudinal direction such that the longitudinal dimension thereof reaches a length equal or close to the longitudinal dimension of the top face sheet 12; the back waist portion is stretched in the lateral direction such that the lateral dimension thereof is a length equal or close to the lateral dimension of the skin-side member 21 and the lateral dimension of the non-skin-side member 22; and the front waist portion 30 is stretched in the lateral direction such that the lateral dimension thereof is a length equal or close to the lateral dimension of the skin-side member 31 and the lateral dimension of the non-skin-side member 32.

Other Embodiments

Although an embodiment of the present invention has been described above, the above embodiment is for facilitating the understanding of the present invention, and is not to be construed as limiting the present invention. The present invention can be modified, improved, etc. without departing from the gist of the present invention, and equivalents of the present invention are also encompassed within the present invention. For example, modifications such as the following can be made.

Although the above embodiment illustrates the so-called three piece type of disposable diaper 1 as an example of the absorbent article, there is no limitation whatsoever to this. For example, the absorbent article may be a two piece type of disposable diaper including: a first component is an exterior sheet including a back waist portion and a front waist portion that are connected via a crotch portion as a single unit; and a second component is an absorbent main body that is fixed to the skin-side surface of the exterior sheet.

The above embodiment describes an example in which the target region 34 has loops, the fastening portion 41 has hooks, and the fastening portion 41 is fastened to the target region 34 by the loops becoming caught on the hooks. However, the configurations of the target region 34 and the fastening portion 41 are not limited to the above example. For example, at least one of the target region 34 and the fastening portion 41 may be provided with adhesiveness on its surface, and they may be fastened by adhering this adhesive member to the surface of the other member.

The above embodiment describes the state where the fastening member 40 projects in a lateral direction from the back waist portion 20 when the diaper is put on. However, the fastening member 40 may be folded when the disposable diaper 1 is manufactured, or the fastening member 40 may be provisionally connected to the front waist portion 30 by perforations.

Also, in the above embodiment, although the elastic region X for ensuring the fit of the diaper 1 is provided, a configuration is possible in which the elastic region X is provided in only the upper end portion of the back waist portion 20. Even with this configuration, it is possible to ensure a necessary fit for the waist opening 1HB of the diaper 1.

In the above embodiment, although the elastic strings 23 and 33 are used as the elastic members, there is no limitation to this. It is possible to use a nonwoven fabric that has stretchability, for example.

In the above embodiment, although the elastic strings 23 and 33 are not provided in the overlapping regions of the back waist portion 20 and the front waist portion 30 in which they overlap with the absorbent body 11, there is no limitation to this. The elastic strings 23 and 33 may be provided in the regions overlapping with the absorbent body 11. By not providing the elastic strings 23 and 33 in the regions overlapping with the absorbent body 11, it is possible to reduce the risk of the absorbent body 11 deformed due to stretching and contracting of the elastic strings 23 and 33. However, by providing the elastic strings 23 and 33 in the regions overlapping with the absorbent body 11, it is possible to improve the fit of the absorbent main body 10 through stretching force.

The invention claimed is:

1. An absorbent article having a longitudinal direction, a lateral direction intersecting the longitudinal direction, and a front-back direction intersecting the longitudinal direction and the lateral direction, the absorbent article comprising:
   a front waist portion extending along the lateral direction;
   a back waist portion extending along the lateral direction; and
   a crotch portion provided between the front waist portion and the back waist portion,
   wherein
   a lateral end portion of the back waist portion on a first side of the absorbent article and a lateral end portion of the front waist portion on the first side are joined by a first joining portion,
   the back waist portion has a fastening portion provided on a second side of the absorbent article opposite to the first side in the lateral direction, the fastening portion being configured to be fastened to the front waist portion when putting on the absorbent article,
   the front waist portion has a target region, the target region being a region to which the fastening portion is to be fastened,
   the crotch portion has a central line that bisects a dimension of the crotch portion in the lateral direction,
   a lateral end of the target region on the first side is located, in the lateral direction, between the lateral end portion of the front waist portion and the central line of the crotch portion,
   when putting on the absorbent article, a first leg opening is formed on the first side of the absorbent article and a second leg opening is not formed on the second side of the absorbent article, and
   the absorbent article is configured such that the second leg opening is formed by fastening the fastening portion to the target region while one of a wearer's legs has been inserted through the first leg opening.

2. The absorbent article according to claim 1, wherein the lateral end of the target region on the first side is located away from the central line of the crotch portion by a distance equal to a length of the fastening portion in the lateral direction.

3. The absorbent article according to claim 1, wherein
the front waist portion has a further lateral end portion on the second side of the absorbent article,
a lateral end of the target region on the second side is located, in the lateral direction, between the central line of the crotch portion and the further lateral end portion of the front waist portion on the second side of the absorbent article, and
the lateral end of the target portion on the second side is located away from the further lateral end portion of the front waist portion on the second side by a distance equal to a length of the fastening portion in the lateral direction.

4. The absorbent article according to claim 3, wherein
the crotch portion has a lateral end on the second side of the absorbent article, and
the lateral end of the target region on the second side is located between the central line of the crotch portion and the lateral end of the crotch portion.

5. The absorbent article according to claim 1, wherein
the front waist portion has an elastic region,
the elastic region is provided in at least a part of a region between the lateral end portion of the front waist portion on the first side and the central line of the crotch portion, and
the elastic region is stretchable and contractible in the lateral direction.

6. The absorbent article according to claim 5, wherein
the elastic region provided in the front waist portion does not exert on the target region a force for causing the target region to contract in the lateral direction.

7. The absorbent article according to claim 1, wherein
an elastic region is provided in at least a part of the back waist portion, and
the elastic region is stretchable and contractible in the lateral direction.

8. The absorbent article according to claim 7, wherein
the elastic region provided in the back waist portion does not exert on the fastening portion a force for causing the fastening portion to contract in the lateral direction.

9. The absorbent article according to claim 1, wherein
a longitudinal length of the fastening portion is shorter than a longitudinal length of the first joining portion.

10. The absorbent article according to claim 1, wherein
a leg-gather elastic member is provided in each of two lateral end portions of the crotch portion,
the leg-gather elastic member is stretchable and contractible in the longitudinal direction, and
a longitudinal range on which the leg-gather elastic member exerts its elastic force does not overlap with the fastening portion.

\* \* \* \* \*